US012016607B2

(12) United States Patent
Kollmann et al.

(10) Patent No.: US 12,016,607 B2
(45) Date of Patent: Jun. 25, 2024

(54) CRYOPROBE FOR MAGNETIC RESONANCE IMAGING

(71) Applicant: Biocompatibles UK Limited, Camberley (GB)

(72) Inventors: Daniel T. Kollmann, Andover, MN (US); Andrew Kevin Zachman, St. Michael, MN (US); Satish Ramadhyani, Minneapolis, MN (US); Oleg Chernihovsky, Benyamina (IL); Dror Trumer, Hadera (IL)

(73) Assignee: Biocompatibles UK Limited, Camberley (GB)

( * ) Notice: Subject to any disclaimer, the term of this patent is extended or adjusted under 35 U.S.C. 154(b) by 1154 days.

(21) Appl. No.: 16/189,182

(22) Filed: Nov. 13, 2018

(65) Prior Publication Data

US 2019/0142491 A1    May 16, 2019

Related U.S. Application Data

(60) Provisional application No. 62/585,279, filed on Nov. 13, 2017.

(51) Int. Cl.
*A61B 18/02*    (2006.01)
*A61B 18/00*    (2006.01)
(Continued)

(52) U.S. Cl.
CPC ............ *A61B 18/02* (2013.01); *G01R 33/285* (2013.01); *A61B 2018/00041* (2013.01);
(Continued)

(58) Field of Classification Search
None
See application file for complete search history.

(56) References Cited

U.S. PATENT DOCUMENTS 3,910,277 A    10/1975  Zimmer
4,444,156 A    4/1984   Iwasaki et al.
(Continued)

FOREIGN PATENT DOCUMENTS

CA    1144223 A    4/1983
CA    2261177 C    5/2007
(Continued)

OTHER PUBLICATIONS

International Search Report and Written Opinion received for PCT Patent Application No. PCT/IB2018/058747, dated Feb. 28, 2019, 14 pages.
(Continued)

*Primary Examiner* — Sean W Collins
*Assistant Examiner* — Nora W Rhodes
(74) *Attorney, Agent, or Firm* — Pauly, DeVries Smith & Deffner LLC (57) ABSTRACT

A cryoprobe is disclosed comprising a probe shaft made of a low magnetic susceptibility material and an electrical resistance heater comprising counter-wound helical coils located within the probe shaft. The counter-wound helical coils are formed by a single wire counter-wound to form a first set of coils wound in a direction counter to a second set of coils, such that when current is supplied to the electrical resistance heater, a first magnetic field generated by the first set of coils is opposite to a second magnetic field generated by the second set of coils. The electrical resistance heater can heat, thaw, and/or cauterize tissue. The electrical resistance heater can be made of a low magnetic susceptibility material so as to resistively heat tissue concurrently during magnetic resonance imaging (MRI). A method of electrically heating a tissue in conjunction with MRI, and a method of imaging a cryoprobe using MRI is also disclosed.

25 Claims, 5 Drawing Sheets

(51) Int. Cl.
   *A61B 18/08* (2006.01)
   *G01R 33/28* (2006.01)
(52) U.S. Cl.
   CPC .............. *A61B 2018/00791* (2013.01); *A61B 2018/0212* (2013.01); *A61B 2018/0262* (2013.01); *A61B 2018/0293* (2013.01); *A61B 18/08* (2013.01)

(56) References Cited

U.S. PATENT DOCUMENTS

| | | | |
|---|---|---|---|
| 4,506,235 | A | 3/1985 | Mayer |
| 4,600,218 | A | 7/1986 | Ross et al. |
| 4,602,809 | A | 7/1986 | Ross et al. |
| 4,862,697 | A | 9/1989 | Tugal et al. |
| 4,978,920 | A | 12/1990 | Mansfield et al. |
| 5,280,247 | A | 1/1994 | Meester et al. |
| 5,522,870 | A | 6/1996 | Ben-Zion |
| 5,603,221 | A | 2/1997 | Maytal |
| 5,800,487 | A | 9/1998 | Mikus et al. |
| 5,800,488 | A | 9/1998 | Crockett |
| 5,916,212 | A | 6/1999 | Baust et al. |
| 5,957,963 | A * | 9/1999 | Dobak, III ............... A61F 7/12 607/104 |
| 6,074,412 | A | 6/2000 | Mikus et al. |
| 6,270,476 | B1 | 8/2001 | Santoianni et al. |
| 6,505,629 | B1 | 1/2003 | Mikus et al. |
| 7,846,154 | B2 | 12/2010 | Bliweis et al. |
| 7,850,682 | B2 | 12/2010 | Amir et al. |
| 8,066,697 | B2 | 11/2011 | Zvuloni et al. |
| 2002/0111615 | A1 | 8/2002 | Cosman et al. |
| 2003/0055416 | A1 | 3/2003 | Damasco et al. |
| 2004/0210212 | A1 | 10/2004 | Maurice |
| 2005/0010200 | A1 | 1/2005 | Damasco et al. |
| 2005/0228367 | A1 | 10/2005 | Abboud et al. |
| 2006/0122590 | A1 | 6/2006 | Bliweis et al. |
| 2006/0155267 | A1 * | 7/2006 | Berzak ............... A61B 18/02 606/20 |
| 2007/0149959 | A1 | 6/2007 | DeLonzor et al. |
| 2008/0085021 | A1 * | 4/2008 | Shim ............... G21K 1/00 381/189 |
| 2009/0292280 | A1 | 11/2009 | Cytron et al. |
| 2010/0114275 | A1 | 5/2010 | Min |
| 2010/0241114 | A1 * | 9/2010 | Privitera ............... A61B 18/02 606/21 |
| 2010/0256620 | A1 | 10/2010 | Maytal |
| 2011/0022040 | A1 | 1/2011 | Geiselhart |
| 2011/0264084 | A1 | 10/2011 | Reid |
| 2012/0065630 | A1 | 3/2012 | Berzak et al. |
| 2012/0089136 | A1 | 4/2012 | Levin et al. |
| 2012/0265452 | A1 | 10/2012 | Ramadhyani et al. |
| 2012/0289953 | A1 | 11/2012 | Berzak et al. |
| 2013/0204241 | A1 | 8/2013 | Baust |
| 2014/0024909 | A1 | 1/2014 | Vij et al. |
| 2014/0135754 | A1 | 5/2014 | Berzak et al. |
| 2014/0194863 | A1 | 7/2014 | Berzak et al. |
| 2014/0232103 | A1 | 8/2014 | Waugh |
| 2014/0265684 | A1 | 9/2014 | Wiese |
| 2015/0293192 | A1 | 10/2015 | Schmidt et al. |
| 2016/0242835 | A1 | 8/2016 | Ramadhyani et al. |
| 2016/0367305 | A1 | 12/2016 | Hareland |
| 2019/0328273 | A1 | 10/2019 | Bonyak et al. |
| 2021/0369319 | A1 * | 12/2021 | Sprain ............... A61B 34/20 |

FOREIGN PATENT DOCUMENTS

| | | |
|---|---|---|
| CN | 107028653 A | 8/2017 |
| EP | 0087371 A2 | 8/1983 |
| EP | 925045 B1 | 4/2003 |
| GB | 2336781 A | 11/1999 |
| JP | 10-272118 A | 10/1998 |
| JP | 10-328157 A | 12/1998 |
| JP | 2001-228227 A | 8/2001 |
| JP | 2007-527729 A | 10/2007 |
| WO | 2005000106 A2 | 1/2005 |
| WO | 2007/073493 A2 | 6/2007 |
| WO | 2014144626 A2 | 9/2014 |

OTHER PUBLICATIONS

"Response to Examiner's Report," for Australian Patent Application No. 2021266350 filed Dec. 4, 2023 (14 pages).

* cited by examiner

CRYOPROBE FOR MAGNETIC RESONANCE IMAGING

CROSS REFERENCE TO RELATED APPLICATION

This application claims the benefit of U.S. Provisional Application No. 62/585,279, filed Nov. 13, 2017, the content of which is hereby incorporated by reference in its entirety.

BACKGROUND

Cryosurgical systems comprise one or more cryoprobe connected to one or more cryofluid sources. Such systems are described in the commonly-assigned patent, U.S. Pat. No. 8,066,697 and in published application, U.S. Pub. No. 2010/0256620 A1, the disclosure of which is hereby incorporated by reference in its entirety. In such cryosurgical systems, a cryofluid can be delivered from a cryofluid source to one or more cryoprobes. The cryoprobe can be cooled as a result of expansion of the cryofluid, thereby freezing tissue in the vicinity of a tip of the cryoprobe.

Some such cryosurgical systems may use Magnetic-Resonance Imaging for imaging a patient, for instance to guide the cryoprobes during insertion and/or to obtain images of anatomical features (e.g., tissue, tumor, and the like). An example of such systems can be found in U.S. Pat. No. 7,850,682, the disclosure of which is hereby incorporated by reference. Such systems may be desirable in situations where other imaging systems (such as Computed Tomography) may not be suitable (for instance, if exposure to radiation is not desired).

Some cryosurgical systems include an electrical heater (in the form of a high resistance wire) positioned within the probe shaft of each cryoprobe to thaw tissue after freezing to facilitate removal of the cryoprobe. In such systems, placement of cryosurgical system having metallic components (e.g., probe shaft or heater wire) with high magnetic susceptibility adjacent to a MRI system may result in imaging artifacts that distort images of the patient and/or cryoprobe. In addition, wound heater wires may lead to solenoidal effects and/or torque on the probe.

SUMMARY

In an aspect, this disclosure provides a cryoprobe, comprising a probe shaft made of a first material and an electrical resistance heater comprising counter-wound helical coils located within the probe shaft. The counter-wound helical coils are formed by a single wire counter-wound about a cryofluid supply tube to form a first set of coils wound in a direction counter to a second set of coils, such that when current is supplied to the electrical resistance heater, a first magnetic field generated by the first set of coils is opposite to a second magnetic field generated by the second set of coils, the electrical resistance heater being made of a second material so as to heat and thereby thaw, and/or cauterize tissue when current is supplied thereto. The electrical resistance heater can be operable to provide electrical resistive heating of tissue concurrently during magnetic resonance imaging (MRI) of the patient.

In another aspect, a method of electrically heating a tissue with a cryoprobe in conjunction with magnetic resonance imaging, comprises the step of providing a cryoprobe according to any of the disclosed embodiments. The method may involve the step of placing a patient, including the patient's target tissue, inside a bore of a MRI system. The method may include inserting the distal section of the cryoprobe into the patient. The method may further include imaging the patient's target tissue, via the MRI system, with the cryoprobe inserted into the patient. The method may involve heating the cryoprobe via the electrical resistance heater concurrently with the MRI imaging.

In a further aspect, a method of imaging a cryoprobe using magnetic resonance imaging (MRI), comprises the step of providing a cryoprobe according to any of the disclosed embodiments. The method may involve the step of providing a magnetic resonance (MR) scanner. The method may involve the step of heating the cryoprobe via the electrical resistance heater by supplying current thereto. The method may further involve the step of generating magnetic resonance (MR) signals for imaging the cryoprobe concurrently when the cryoprobe is being heated.

Certain embodiments of the present disclosure include the following numbered embodiments:

1. A cryoprobe, comprising:
    a probe shaft having a proximal section and a distal section opposite to the proximal section, the distal section being insertable into a patient, the probe shaft being made of a first material having a magnetic susceptibility of less than about 0.001 in S.I. units;
    a cryofluid supply tube located within the probe shaft, the cryofluid supply tube being configured to receive cryofluid from a cryofluid source, the cryofluid supply tube being configured to supply the cryofluid toward the distal section for cooling and/or freezing the patient's tissue; and
    an electrical resistance heater comprising resistive elements having counter-wound helical coils located within the probe shaft, the counter-wound helical coils comprising a first set of coils wound in a direction counter to a second set of coils, a number of coils of the first set of coils being balanced by a number of coils of the second set of coils such that when current is supplied to the electrical resistance heater, a first magnetic field generated by the first set of coils is counteracted and/or opposite to a second magnetic field generated by the second set of coils, the electrical resistance heater being made of a second material having a magnetic susceptibility less than about 0.0005 in S.I. units, the electrical resistance heater being configured to heat and thereby thaw, and/or cauterize tissue, when current is supplied thereto,
    whereby the electrical resistance heater is configured to provide electrical resistive heating of tissue when positioned in a magnet room of a magnetic resonance imaging (MRI) system.
2. The cryoprobe of embodiment 1, wherein the first set of coils and the second set of coils are each configured to generate heat when current is supplied to the electrical resistance heater.
3. The cryoprobe of embodiment 1 or 2, wherein the electrical resistance heater comprises a single wire made of the second material, the single wire being wound in a first direction to form the first set of coils, the single wire being wound in a second direction to form the second set of coils, the first direction being counter to the second direction.
4. The cryoprobe of embodiment 3 or any previous embodiment, wherein the single wire is wound as a continuous loop having a looped section, so as to form the first set of coils and the second set of coils.

5. The cryoprobe of embodiment 4 or any previous embodiment, wherein the looped section is positioned in or near the distal section of the probe shaft.
6. The cryoprobe of embodiment 1 or any previous embodiment, wherein the probe shaft is made of Inconel alloys.
7. The cryoprobe of embodiment 6 or any previous embodiment, wherein the second material is titanium.
8. The cryoprobe of embodiment 1 or any previous embodiment, wherein the electrical resistance heater is configured to receive electric current when the cryoprobe is connected to a MRI scanner.
9. The cryoprobe of embodiment 8 or any previous embodiment, wherein the first magnetic field associated with the first set of coils counteract the second magnetic field associated with the second set of coils when current is passing through the electrical resistance heater and the cryoprobe is proximal to the MRI scanner, so as to reduce artifacts in a MRI image generated by the MRI scanner.
10. The cryoprobe of embodiment 8 or any previous embodiment, wherein the counter-wound helical coils permitting cancellation of a first force of the first set of coils and a second force of the second set of coils when current is passing through the electrical resistance heater when the cryoprobe is proximal to the MRI scanner so as to reduce torque on the cryoprobe.
11. The cryoprobe of embodiment 1 or any previous embodiment, wherein each of the cryofluid supply tube and the electrical resistance heater is coaxial with the probe shaft, the electrical resistance heater being radially offset from an inner wall of the probe shaft so as to form an annular return lumen, the annular return lumen permitting return of the cryofluid from the distal section toward the proximal section.
12. The cryoprobe of embodiment 1 or any previous embodiment, wherein the electrical resistance heater is connectable to a temperature measurement apparatus so as to determine temperature of the electrical resistance heater when current is supplied therethrough.
13. A method of electrically heating a cryoprobe in conjunction with magnetic resonance imaging, comprising:
providing a cryoprobe, comprising:
a probe shaft having a proximal section and a distal section opposite to the proximal section, the probe shaft being made of a first material having a magnetic susceptibility less than about 0.001 in S.I. units, and
an electrical resistance heater comprising resistive elements having counter-wound helical coils, the counter-wound helical coils comprising a first set of coils wound in a direction counter to a second set of coils, the electrical resistance heater being made of a second material having a magnetic susceptibility less than about 0.0005 in S.I. units;
placing a patient, including the patient's target tissue, inside a bore of a MRI system;
inserting the distal section of the cryoprobe into the patient;
heating the cryoprobe via the electrical resistance heater when the patient is placed in the bore of the MRI system whereby a first magnetic field associated with the first set of coils being counteracted by and/or is opposite to a second magnetic field associated with the second set of coils.
14. The method of embodiment 13 or any previous embodiment, further comprising thawing the tissue by supplying current to the electrical resistance heater so as to achieve a tissue temperature of between about 60° C. and about 90° C.
15. The method of embodiment 14 or any previous embodiment, further comprising cauterizing the tissue by supplying current to the electrical resistance heater so as to achieve a tissue temperature of about 100° C.
16. The method of embodiment 13 or any previous embodiment, further comprising connecting the electrical resistance heater to a temperature measurement system, and measuring temperature of the electrical resistance heater when current is supplied thereto.
17. The method of embodiment 13 or any previous embodiment, further comprising position the cryoprobe in a MRI room comprising the MRI system.
18. The method of embodiment 13 or any previous embodiment, further comprising cooling and/or freezing tissue by supplying cryofluid to the cryoprobe.
19. The method of embodiment 13 or any previous embodiment, further comprising cancelling the first magnetic field associated with the first set of coils with the second magnetic field associated with the second set of coils when current is passing through the electrical resistance heater when the cryoprobe is proximal to a MRI scanner, and thereby suppressing artifacts in a MRI image generated by the MRI scanner.
20. The method of embodiment 19 or any previous embodiment, further comprising cancelling a first force of the first set of coils with the a second force of the second set of coils when current is passing through the electrical resistance heater when the cryoprobe is proximal to the MRI scanner, and thereby reducing torque on the cryoprobe.
21. A method of imaging a cryoprobe using magnetic resonance imaging (MRI), comprising:
providing a cryoprobe, comprising:
a probe shaft having a proximal section and a distal section opposite to the proximal section, the probe shaft being made of a first material having a magnetic susceptibility less than about 0.001 in S.I. units, and
an electrical resistance heater comprising resistive elements having counter-wound helical coils, the counter-wound helical coils comprising a first set of coils wound in a direction counter to a second set of coils, the electrical resistance heater being made of a second material having a magnetic susceptibility less than about 0.005 in S.I. units;
providing a magnetic resonance (MR) scanner;
heating the cryoprobe via the electrical resistance heater by supplying current thereto;
generating magnetic resonance (MR) signals; and
imaging the cryoprobe concurrently when the cryoprobe is being heated, whereby a first magnetic field generated by the first set of coils is counteracted by and/or opposite to a second magnetic field generated by the second set of coils.
22. The cryoprobe of embodiment 1 or any previous embodiment, wherein the first material has a magnetic susceptibility of less than or equal to about 0.0006 in S.I. units.
23. The cryoprobe of embodiment 1 or any previous embodiment, wherein the second material has a magnetic susceptibility of less than or equal to about 0.0002 in S.I. units.

23. The cryoprobe of embodiment 1 or any previous embodiment, wherein the first material has a magnetic susceptibility of between about 0.0002 and about 0.001 in S.I. units.

24. The cryoprobe of embodiment 1, wherein the second material has a magnetic susceptibility of between about 0.0001 and about 0.0005 in S.I. units.

The details of one or more examples are set forth in the accompanying drawings and the description below. Other features, objects, and advantages will be apparent from the description and drawings, and from the claims.

DETAILED DESCRIPTION

Cryosurgical systems can be used for cryoablating target tissues (e.g., a tumor). Typically, such systems include one or more cryoprobes, one or more cryofluid sources and a controller. The cryofluid sources can supply gases such as argon, nitrogen, air, krypton, $CO_2$, $CF_4$, xenon, and various other gases that are capable of reaching cryogenic temperatures (e.g., temperatures below 190 Kelvin) when expanded from pressures greater than about 1000 psi. As used herein, "cryofluid" can refer to any fluid that reaches low temperatures (e.g., below 190 Kelvin) when expanded from pressures greater than about 1000 psi (e.g., typically around 3500 psi). The cryosurgical system can also include a controller having one or more sensors, flow meters, timers, analog/digital converters, wired or wireless communication modules, etc. Additionally, the controller can also regulate the flow rate, temperature and pressure of cryofluid supplied to the cryoprobe.

During cryosurgery, for instance, a surgeon may deploy one or more cryoprobes to cryoablate a target area of a patient anatomy by placing the cryoprobe at or near the target area of the patient anatomy. In one example, cryoprobe utilizes the Joule-Thomson effect to produce cooling or heating. In such cases, a cryofluid expands in the cryoprobe from a higher pressure to a lower pressure. Expansion of the cryofluid results in temperatures at or below those necessary for cryoablating a tissue in the vicinity of the tip of the cryoprobe. Heat transfer between the expanded cryofluid and the outer walls of the cryoprobe can be used to form an iceball, and consequently cryoablate the tissue.

Figure 1:
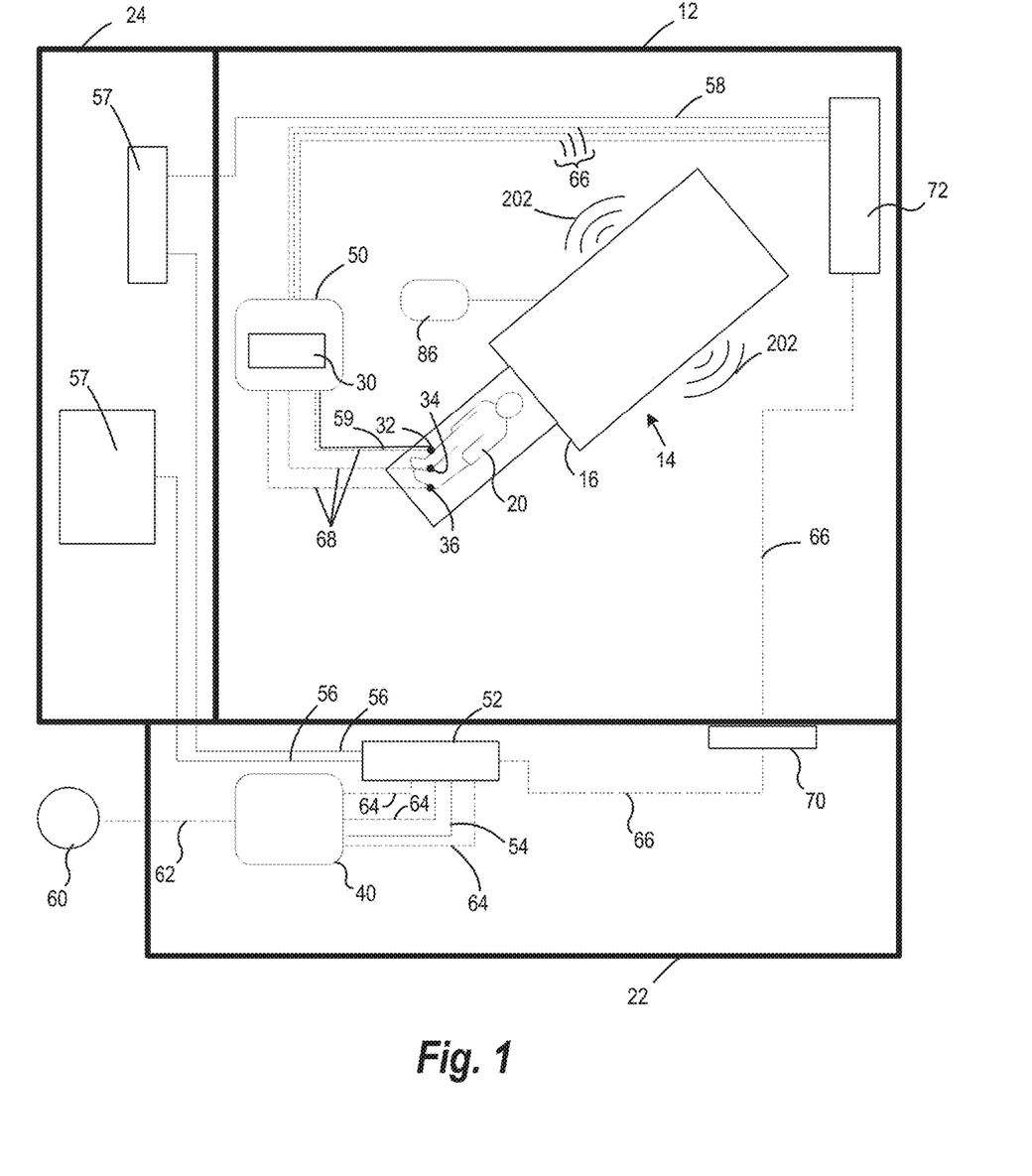
FIG. 1 is a schematic of a Magnetic Resonance Imaging (hereinafter "MRI")-guided cryosurgery system according to a non-limiting exemplary embodiment.

FIG. 1 is a schematic of a Magnetic Resonance Imaging (hereinafter "MRI")-guided cryosurgery system 10 according to a non-limiting exemplary embodiment. The system of FIG. 1 can include components of a MRI system positioned inside a magnet room 12. The MRI system comprises a MRI scanner 14 having a MRI magnet 16 in the form of a bore for accommodating a patient 20. The MRI magnet 16 (bore) can be of open or closed type, and can include access ports to allow a surgeon to access the patient 20. The MRI magnet 16 can also have electrical connection lines (illustrated by solid lines) and/or mechanical and/or fluid connection lines (illustrated by dashed lines) in FIG. 1 for connecting to various electrical, control and/or cryoablation systems as will be described further below. The system can also include a control room 22 electrically isolated from the magnet room 12, and an equipment room 24. The MRI system may image the patient before insertion of surgical tools 32 to visualize patient areas of interest, such as a tumor or a patient cavity. Further, imaging may be performed during insertion to guide the surgical tool to the intended location inside the patient. Additionally, imaging may be performed after insertion and during surgery, as well as after surgery.

Continuing with FIG. 1, in a non-limiting exemplary embodiment, the connection lines may terminate in one or more surgical tools 32, such as cryoprobes insertable inside a patient 20. Accordingly, in some such examples, the system may include a connector interface 30 placed inside the magnet room 12 for permitting connection of one or more surgical tools 32, 34, 36 to other components of the cryoablation systems that may be placed outside the magnet room 12 (for instance, in a control room 22 or an equipment room 24). For instance, the system may include electrical connection lines 54 and fluid connection lines 62 extending from the control room 22 to the magnet room 12, so as to operatively connect a control system 40 to the surgical tools 32. The connector interface 30 can, in some advantageous embodiments, be provided on a mobile console 50 positioned proximal to the magnet to permit a plurality of surgical tools 32 to be directly or indirectly (e.g., electrically and/or fluidly) connected to the control system 40 positioned outside the magnet room 12 (e.g., in the control room 22).

The electrical and fluid connections between the control system 40 and the surgical tools 32 will be described according to an example embodiment. The control system 40 can be electrically connected to a junction box 52 located external to the magnet room 12 by way of a first set of electrical connection lines 54. Further, the junction box 52 can include a second set of electrical connection lines 56 to connect to electrical and/or imaging equipment 57 (such as an imaging router and electrical filters) located external to the magnet room 12 (for instance, within the equipment room 24). A third set of electrical connection lines 58 may connect the electrical and/or imaging equipment 57 to the connector interface 30 and/or mobile console 50 located inside the magnet room 12. The junction box 52 can permit removable electrical connection between components in the magnet room 12 and components in the electrical and/or control rooms.

Referring again to FIG. 1, in some examples, the system may be used to perform cryosurgical procedures (e.g., cryoablation). Accordingly, in some examples, the system may include one or more cryofluid sources 60. The cryofluid source can be a liquid or gas container that can provide a fluid at cryogenic temperatures and pressures to surgical tools 32 (e.g., cryoprobes). The cryofluid source can be a cooling gas such as argon, nitrogen, air, krypton, $CF_4$, xenon, or $N_2O$.

As illustrated in FIG. 1, the cryofluid source is positioned outside the magnet room 12 and is fluidly connectable to the control system 40 by way of a first set of fluid connection lines 62. The control system 40 in turn can be fluidly connected to the connector interface 30 and/or mobile console 50 by way of a second set of fluid connection lines 64 and a third set of fluid connection lines 66. A fourth set of fluid connection lines 68 can fluidly connect the surgical tools 32 (e.g., cryoprobes) to the connector interface 30 and/or mobile console 50. The fluid lines can be flexible and/or detachable and may include other fluid components to regulate pressure of fluid passing therethrough. Fluid from the cryofluid source may thus be conveyed by the set of fluid connection lines 62, 64, 66 and 68 to the surgical tools 32. Optionally, the system can include a fluid connection panel 70 electrically isolated from the magnet room 12 so as to permit fluid connections between components present in the magnet room 12 and those in the control room 22. Similarly, an electrical connection panel 72 can facilitate electrical connections between components present in the magnet room 12 and those in the control room 22 and/or electrical room.

Referring back to FIG. 1, the system also includes a MRI display 86 operatively coupled to the MRI scanner 14 and positioned within the magnet room 12 for displaying an image representative of an anatomical feature of a patient 20 so as to provide guidance to a surgeon during surgery. The MRI display 86 can be operatively coupled to electrical and/or imaging components in the equipment room 24 and the control system 40 located within the control room 22. Such a configuration may display information relating to the operating conditions of the overall system. In such cases, advantageously, the MRI display 86 may enable a surgeon to select a desired image, for example, to monitor the progress of the surgical process, images relating to MRI guidance and/or current information relating to one or more surgical tools 32. Optionally, more than one display may be provided in the magnet room 12 to permit simultaneous visualization of various aspects of the surgical procedure.

Figure 2:
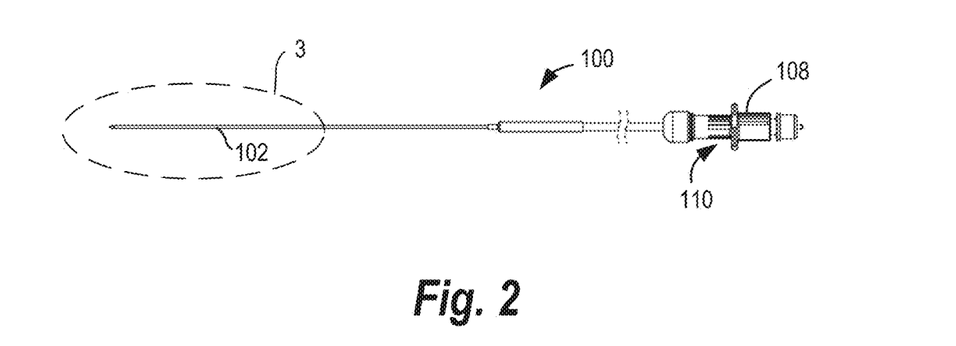
FIG. 2 is a general view of a cryoprobe connectable to the control system of FIG. 2 according to a non-limiting exemplary embodiment.
Figure 3:
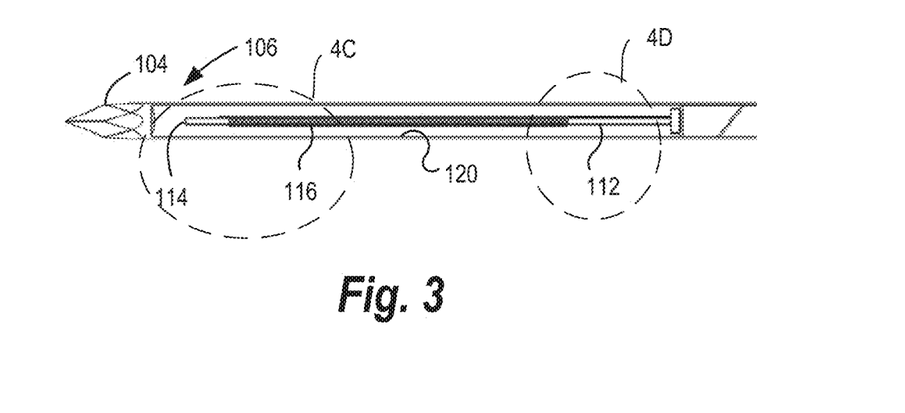
FIG. 3 is a sectional front view of the cryoprobe of FIG. 2.

As described earlier, the surgical tool can be a cryoprobe 100 in a non-limiting exemplary embodiment. FIG. 2 is a general view of one such cryoprobe 100 and FIG. 3 is a sectional front view of the cryoprobe 100 of FIG. 2. Referring to FIGS. 3 and 4, the cryoprobe 100 can include an elongate body. Components of the cryoprobe 100 can be located within a probe shaft 102. The cryoprobe can, in some cases, be a cryoneedle, in which case, components of the cryoneedle may be arranged interior to a trocar. The probe shaft 102 can terminate in a distal operating tip 104 disposed at a distal section 106 of the cryoprobe 100 for penetrating through tissues of a patient 20 during deployment. In embodiments where the cryoprobe is configured as a cryoneedle, the distal operating tip 104 can penetrate the patient's skin. In alternate embodiments, the cryoprobe can be a flexible probe, and may be inserted by way of a catheter. A proximal coupler 108 can facilitate connections of the cryoprobe 100 to a connector interface 30, control system 40 and/or cryofluid source.

The probe shaft 102 can be of substantially thin cross section to allow deployment in tissues of a patient 20. In an example, the cryoprobe can be a cryoneedle, having a probe shaft 102 outer diameter of about 2.1 millimeters. Other dimensions of the probe shaft 102 are also contemplated. For example, the probe shaft 102 can have an outer diameter of between about 1.5 millimeters and about 2.4 millimeters. In addition, in embodiments where the cryoprobe is a cryoneedle, the distal operating tip 104 can be made of a pliant material so as to be flexible (e.g., relative to the proximal portion of the cryoprobe 100) for penetrating soft tissue. Alternatively, a substantial portion of the cryoprobe can be generally flexible and may not pierce the patient skin, and may be flexible (bendable) about its central axis, by a desired angle.

As illustrated by FIG. 3, the cryoprobe 100 includes a cryofluid supply tube 112 extending substantially along its length for providing a high-pressure cryofluid to the distal operating tip 104. The cryofluid supply tube 112 can be positioned coaxially/concentrically within the probe shaft 102. The cryofluid supply tube 112 can be configured to supply a cryofluid for forming iceballs on an outer surface of the probe shaft 102 over the distal section 106. In some cases, the cryofluid supply tube 112 can be a capillary tube.

With continued reference to FIG. 3, in some examples, the cryoprobe 100 includes a cryocooler. For instance, in the illustrated example, the cryofluid supply tube 112 can terminate in a Joule-Thomson orifice 114. The Joule-Thomson orifice 114 can be positioned near the distal operating tip 104, so as to permit cryofluid exiting the Joule-Thomson orifice 114 to expand into an expansion chamber. Accordingly, a high-pressure cryofluid supplied via the cryofluid supply tube 112 exits through the Joule-Thomson orifice 114 and expands in the expansion chamber. As the cryofluid expands in the expansion chamber, it cools rapidly and forms iceballs of different shapes and/or sizes over the outer surface of the distal operating tip 104. The expansion of the cryofluid can be such that when expanded, the cryofluid is colder than the incoming cryofluid. While an exemplary cryocooler such as a Joule-Thomson orifice 114 is illustrated, it should be understood that other types of cryocoolers such as cryogenic dewars, Stirling-type cooler, pulse-tube refrigerator (PTR), Gifford-McMahon (GM) cooler are contemplated within the scope of the present disclosure. Further, as briefly noted above, cryofluids which may be used for cooling include argon, liquid nitrogen, air, krypton, $CF_4$, xenon, or $N_2O$.

Referring again to FIG. 3, in some examples, a heater 116 can optionally be provided within the probe shaft 102 to facilitate thawing and/or cauterizing tissue. In some such examples, the heater 116 may be operated after cooling and iceball formation to thaw frozen tissue to facilitate disengagement of cryoprobe 100 therefrom. An electrical heater 116 can be provided coaxially with the cryofluid supply tube 112 and the probe shaft 102 to facilitate heating the distal section 106 of the cryoprobe 100. Alternatively, the electrical heater 116 can be positioned elsewhere in cryoprobe 100 to heat the distal section 106 of the cryoprobe 100. The electrical heater 116 can be a resistive heater 116, wherein the electrical heater 116 generates heat proportional to the square of the current flow therethrough and the electrical resistance of electrical heater 116. In such cases, as alluded to previously, the control system 40 (shown in FIG. 2) can supply and/or regulate electrical current flow to the electrical heater 116 within the cryoprobe 100.

As described previously with reference to FIG. 1, certain components of the cryoablation system are positionable proximate to MRI system that permits imaging and guidance before, during or after surgery. For instance, the cryoprobes can be connected to the fourth set of electrical connection lines 59 from the mobile console 50, in turn connected to the connector interface 30. In FIG. 1, only a single cryoprobe is electrically connected by connection line 59, however, any number of cryoprobes can be connected to the mobile console 50 using separate connection lines 59 respectively.

In some advantageous embodiments, the outer surface of the distal operating tip 104 can be made of a heat conducting material such as metal for effectively freezing or thawing the patient's tissue while having a low magnetic susceptibility (e.g., relative to conventional probes and/or probe shafts) so to reduce image artifacts in the MRI image. In some such examples, the outer surface of the distal operating tip 104 can be made of a material such as Inconel alloys (e.g., Inconel 625). Other metals and alloys permitting heat exchange between the distal operating tip 104 and the patient tissue while minimizing induced magnetic fields from the MRI system are contemplated within the scope of the present disclosure. In addition, a substantial portion of the probe shaft 102 may comprise a metallic material having a magnetic susceptibility suitable to reduce image artifacts in the MRI image. In some such exemplary embodiments, the probe shaft 102 can comprise a material such as Inconel 625. Further, the probe shaft 102 and the distal operating tip 104 can each be made of materials having magnetic susceptibility not to exceed about-0.001 (in S.I. units), preferably, not to exceed about $6 \times 10^{-4}$ (in S.I. units), and even more preferably, not to exceed about $1 \times 10^{-4}$ (in S.I. units)

In certain aspects illustrated in FIG. 3, the electrical heater 116 can be configured to minimize image artifacts and forces or torques that may develop when exposed to magnetic fields from the MRI system. For instance, in an aspect, the electrical heater 116 can be made of a metal wire 126 having a magnetic susceptibility sufficiently low so as to not develop reactive effects when exposed to magnetic fields from the MRI system. The magnetic susceptibility of the metal wire 126 of the heater 116 may not exceed about $5 \times 10^{-4}$ (in S.I. units), preferably not to exceed about $1.5 \times 10^{-4}$ (in S.I. units), even more preferably not to exceed about $1 \times 10^{-4}$ (in SI units) in some such advantageous examples.] Further, the metal wire 126 (or portions thereof that form resistive elements of the heater 116) can be made of a material such as titanium. The material of the wire used for forming the electric heater 116, while having low magnetic susceptibility, may have a high electrical resistance such that heat is generated when current passes therethrough. A pair of lead wires 142, 144 may attach to terminal ends 128, 129 of the heater wire, to electrically connect the heater 116 to the control system 40 and supply current thereto. In some such examples, the lead wires 142, 144 and the terminal ends 128, 129 of the heater wire may be bonded or otherwise attached to the cryofluid supply tube 112, and spaced apart from the inner surface 120 of the probe shaft 102 so as to electrically isolate the probe shaft 102 (which may be electrically conductive) from the current carrying heater 116.

Figures 4A, 4B:
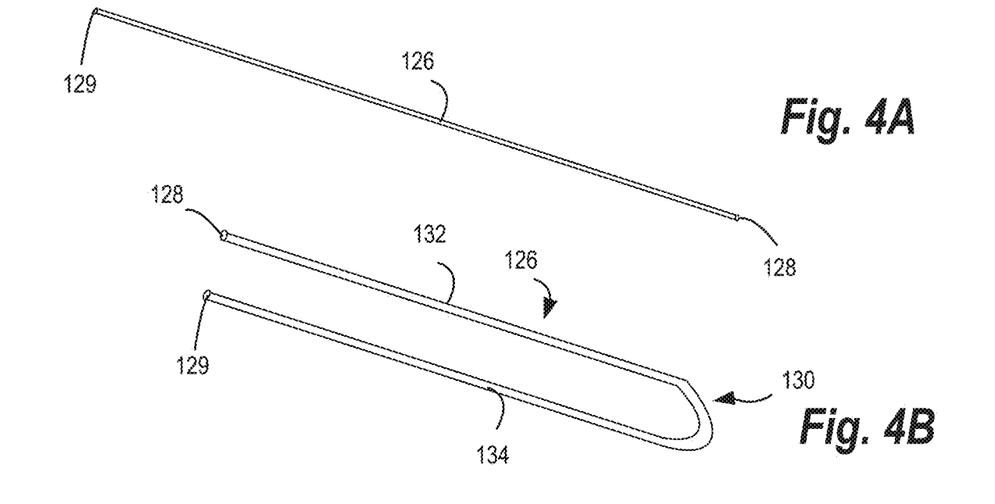
FIG. 4A is a perspective view of a wire used for forming the helical coiled heater of cryoprobe of FIG. 3.
FIG. 4B is another perspective view of the wire used for forming the helical coiled heater of cryoprobe of FIG. 3.
Figure 4C:
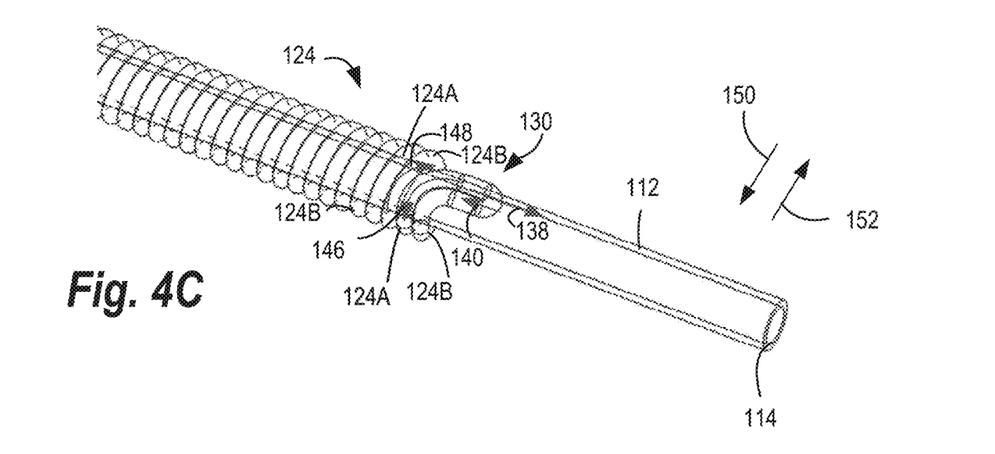
FIG. 4C is an enlarged perspective view of portion 4C that shows the distal section of the cryoprobe illustrated in FIG. 3.
Figure 4D:
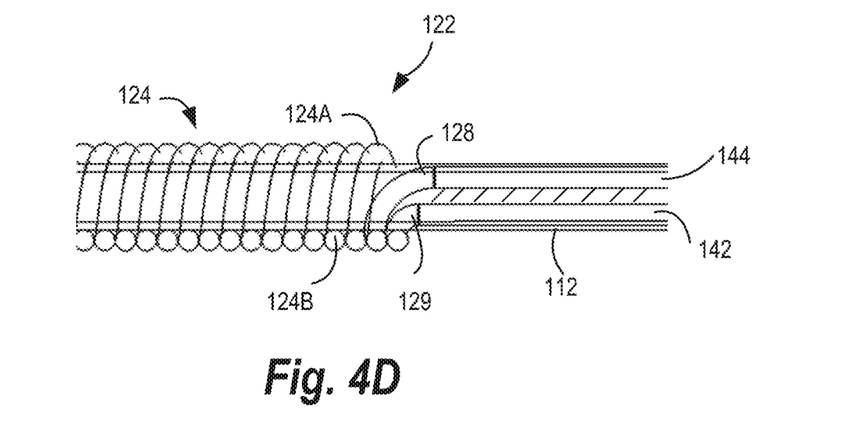
FIG. 4D is an enlarged perspective view of portion 4D that shows a middle section of the cryoprobe illustrated in FIG. 3.

FIGS. 4A and 4B illustrate a perspective view of a heater wire, while FIGS. 4C and 4D illustrate a front perspective view and a front view of the distal section 106 and a middle section 122 of the cryoprobe 100, respectively. The middle section 122 can be between the distal section 106 and the proximal section 110. In FIGS. 4C-4D, the probe shaft 102 has been removed to illustrate interior details of the cryoprobe 100. As illustrated by FIGS. 4A-4D, the electrical heater 116 comprises a portion having resistive elements that include counter-wound helical coils 124. The counter-wound helical coils 124 can be formed from a metal wire 126 (e.g., titanium or other low magnetic susceptibility material). The counter-wound helical coils 124 can include a first set of coils 124A wound in a direction counter to a second set of coils 124B. In an example, the counter-wound helical coils 124 can be wound by taking a single metal wire 126 shown in FIG. 4A, folded to bring opposite terminal ends 128, 129 toward each other, so as to form a U-shaped looped section 130 as shown in FIG. 4B. As shown in FIG. 4C, the U-shaped looped section 130 can be positioned in the distal section 106 and the folded wire can be continuously wound about the cryofluid supply tube 112, by winding legs 132, 134 of the folded wire around the elongate cryofluid supply tube 112. The first set of coils 124A can thus be formed from the first leg 132 in a first direction 138 (for example, to allow current flow along the first direction 138) and the second set of coils 124B can be formed from the second leg 134 in a second direction 140 (for example, to allow the current flow along the second direction 140). For example, if the first set of coils 124A has a counter-clockwise direction when viewed from the front, the second set of coils 124B can have a clockwise direction when viewed from the front, though, the specific direction of winding the first set of coils 124A and the second set of coils 124B may not be construed as limiting.

The electrical heater 116 thus includes resistive elements substantial portions of which are counter wound to form coils 124A, 124B. The resistive elements terminate near ends 128, 129 of the wire. As illustrated in FIG. 4D, the terminal ends 128, 129 of the wire can be connected to a pair of lead wires 142, 144, which in turn can be connected (e.g., directly or indirectly) to the control system 40. The control system 40 can supply and/or regulate current to the electrical heater 116 (e.g., via the lead wires 142, 144). In certain embodiments, the first set of coils 124A and the second set of coils 124B may each carry current, and therefore may each generate heat.

In certain advantageous aspects, the electrical heater 116 illustrated in FIGS. 4A-4D can reduce or eliminate solenoidal effects the heater 116 is energized (e.g., when current is supplied thereto). The current flow may be associated with the heater operation and may be supplied from the control system. As a result of counter winding the wire to form counter-wound coils 124A, 124B, advantageously, magnetic fields associated with the electrical heater 116 when current is supplied to the electrical heater 116 may counteract or offset (e.g., act in an opposite direction to) each other. In an example, when current is supplied to the electrical heater 116, a first magnetic field 146 associated with (e.g., generated by or induced into) the first set of coils 124A can be in a direction opposite to a second magnetic field 148 associated with (e.g., generated by or induced into) the second set of coils 124B. In FIG. 4C, the first magnetic field 146 and the second magnetic field 148 are illustrated by exemplary magnetic field lines (for instance, in accordance with right hand rule). However, the direction of several other magnetic field lines associated with the first magnetic field 146 and the second magnetic field 148 are omitted for clarity. Further, the first magnetic field 146 may be equal in magnitude with the second magnetic field 148 such that the first magnetic field 146 cancels the second magnetic field 148. Accordingly, when current is passing through the electrical heater 116 and the cryoprobe 100 is in the magnet room 12 (e.g., proximal to the MRI scanner), certain solenoidal effects can be reduced or eliminated by certain embodiments of the present disclosure, so as to reduce or eliminate artifacts in a MRI image generated by the MRI system. Additionally, magnetic fields of lower magnitude (relative to the magnetic fields associated with when the heater is a energized) may also include induced current flow into the electrical wire when the MRI scanner is being operated. In this case, if the electrical heater operates simultaneously with the MRI scanner, the magnetic field induced from both the MRI operation may also be reduced or eliminated as a result of counter-wound helical coils and the use of low magnetic susceptibility materials for the probe shaft and the electrical resistance elements of the heater.

Continuing with the previous description, the induced magnetic fields (from MRI operation) and the generated magnetic field (from current supplied to the heater) may not always be aligned with each other, and as can result in a net force or a torque on the probe shaft. Accordingly, in further advantageous aspects, electrical heater 116 illustrated in FIGS. 4A-4D can reduce or eliminate net forces or torques acting on the probe shaft when current is supplied to the electrical heater 116 concurrently when the probe shaft is positioned proximal to the MRI system when the MRI scanner is being operated (e.g., producing magnetic and/or radiofrequency fields). As is apparent, when current passes through the electrical heater 116, and when the heater 116 is exposed to magnetic fields (e.g., generated by MRI scanner), a force (e.g., Lorenz force) may act on the electrical heater 116 as a result of the induced magnetic field acting in a different direction relative to the magnetic field generated by the current-carrying heater wire. The direction of the force may be provided by a right-hand rule. However, as a result of low magnetic susceptibility material used in forming the electrical heater 116, the magnitude of the magnetic force may be lower than those associated with conventional cryoprobes with electric heaters.

In addition, as a result of counter-wound coils 124A, 124B the direction of magnetic forces may be opposite to each other. For instance, the first set of coils 124A may develop a first force 150 and the second set of coils 124B may develop a second force 152 when the coils 124A, 124B carry current and are exposed to a magnetic field (e.g., from the MRI magnet). The first force 150 and the second force 152 (shown for instance, in FIG. 4C as arrows according to right hand rule) may act in directions opposite to each other, such that the first force 150 offsets the second force 152 so as to reduce the net force (and thereby a net torque) associated with the electrical heater 116 that may act on the probe shaft 102. Advantageously, the first force 150 and second force 152 may be equal in magnitude as the first set of coils 124A and the second set of coils 124B are formed from the same (low magnetic susceptibility) material. In such cases, the first force 150 cancels the second force 152, thereby reducing the net force acting on the probe shaft 102 to zero. As a result, the probe shaft 102 may not experience a torque thereon. Such advantageous embodiments may permit using the electrical heater 116 to thaw or cauterize tissue when the cryoprobe 100 is positioned proximal to the MRI scanner (e.g., in the magnet room 12 near the MRI magnet), and/or during operation thereof.

In an aspect, the cryoprobe 100 may include a temperature monitoring and/or control system 40. For instance, the distal operating tip 104 can include at least one thermal sensor for sensing the temperature during the operation of the electrical heater 116. In certain advantageous aspects, the material of the electrical heater 116 can have a positive temperature coefficient of resistance so as to act as a thermal sensor and permit measurement of temperature. Accordingly, in such embodiments, the electrical heater 116 is connectable to a temperature measurement apparatus so as to determine temperature of the electrical resistance heater 116 when current is supplied therethrough. The temperature measurement apparatus may be positioned within the control system 40 (shown in FIG. 1), or be positioned proximal to the cryoprobes in the magnet room. The temperature measurement apparatus may monitor the resistance of the electrical heater 116 when current passes therethrough, and infers the resistance based on the heater 116 material's temperature coefficient of resistance. The control system 40 may also regulate the current to the heater 116 based on the measured temperature, so as to provide a sufficient temperature at the distal tip to perform a desired surgical procedure (e.g., thaw to remove the cryoprobe 100 after a freezing operation, or cauterize tissue).

Figure 5:
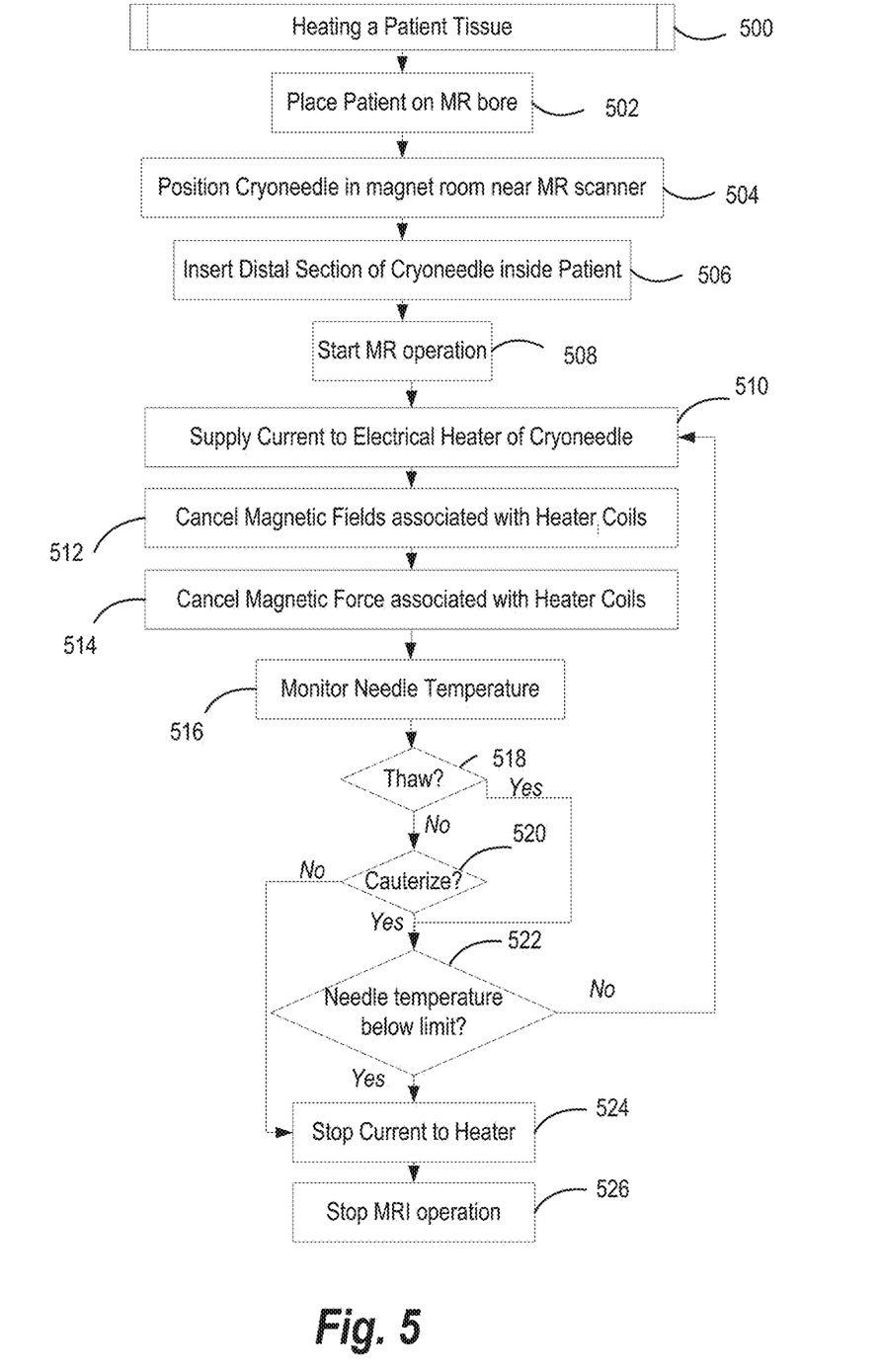
FIG. 5 is a flow chart illustrating a method of heating a patient tissue using the cryoprobe.

FIG. 5 illustrates a method 500 of electrically heating a tissue using a cryoprobe 100 in conjunction with a MRI system. The method illustrated in FIG. 5 can be performed with the cryoprobe 100 according to any of the embodiments described herein. Further, the MRI system usable with the method of FIG. 5 can also be according to any of the embodiments described herein. In step 502, the method involves placing a patient inside the magnet room. The patient may be placed inside the bore either before or after insertion of the cryoprobe inside the patient (e.g., at or near a target tissue). The cryoprobe 100 may be placed in the magnet room at step 504. The distal section 106 of the cryoprobe 100 may be inserted into the patient at step 506. Once the cryoprobe 100 is inside the patient, a heating operation may be performed. Advantageously, the heating operation may be performed concurrently during operation of the MRI system. At this time, at step 508, the MRI system may generate a magnetic field and/or radiofrequency (RF) signals and images the patient's target tissue with the cryoprobe 100 inserted into the patient. At step 510, the cryoprobe 100 may heat tissue. At this time, the control system 40 may supply current to the electrical heater 116 concurrently at the time of MR imaging. In such advantageous embodiments, the low magnetic susceptibility (e.g., non-ferromagnetic) material of the probe shaft 102 and the heater wire, as well as the counter-wound helical coils 124 may mitigate reactive effects such as solenoidal effects (e.g., image artifacts, torqueing, induced magnetic fields, and the like). For instance, the magnetic field and magnetic forces associated with the helical coils 124A, 124B of the electric heater 116 may cancel each other at steps 512 and 514.

The control system 40 may determine the temperature of probe shaft 102 at step 516. In an aspect, the material of the electrical heater 116 may have known temperature coefficient of resistance (e.g., positive temperature coefficient of resistance). Accordingly, the control system 40 may measure or determine the resistance of the electrical heater 116 when it is receiving current and determine the probe shaft 102 temperature.

In certain embodiments, the method can comprise the step of thawing the tissue (at step 518). At step 518, the control system 40 may supply current to the electrical heater 116 so as to achieve a tissue temperature of between about 60° C. and about 90° C. In addition, the method can comprise the step of cauterizing the tissue (at step 520). At step 520, the control system 40 may supply current to the electrical heater 116 so as to achieve a tissue temperature of about 100° C. During thawing or cauterization, the temperature achievable at the distal tip may be measured by a temperature measurement apparatus as described previously. In such cases, the control system 40 may determine (at step 522) if the desired temperature for the surgical operation (thaw or cauterize). If the desired temperature has been achieved (e.g., at the probe shaft 102), the control system 40 may stop supplying current to the heater 116 at step 524. Optionally, systems described herein may perform a cooling and/or freezing operation before or after a thawing or a cauterizing operation. As described previously, the cooling or freezing operation may involve supplying cryofluid to the cryoprobe 100 to form iceballs in the distal section 106 of the cryoprobe 100. Once desired surgical procedures have been completed, the MRI operation may be stopped at step 526.

Figure 6:
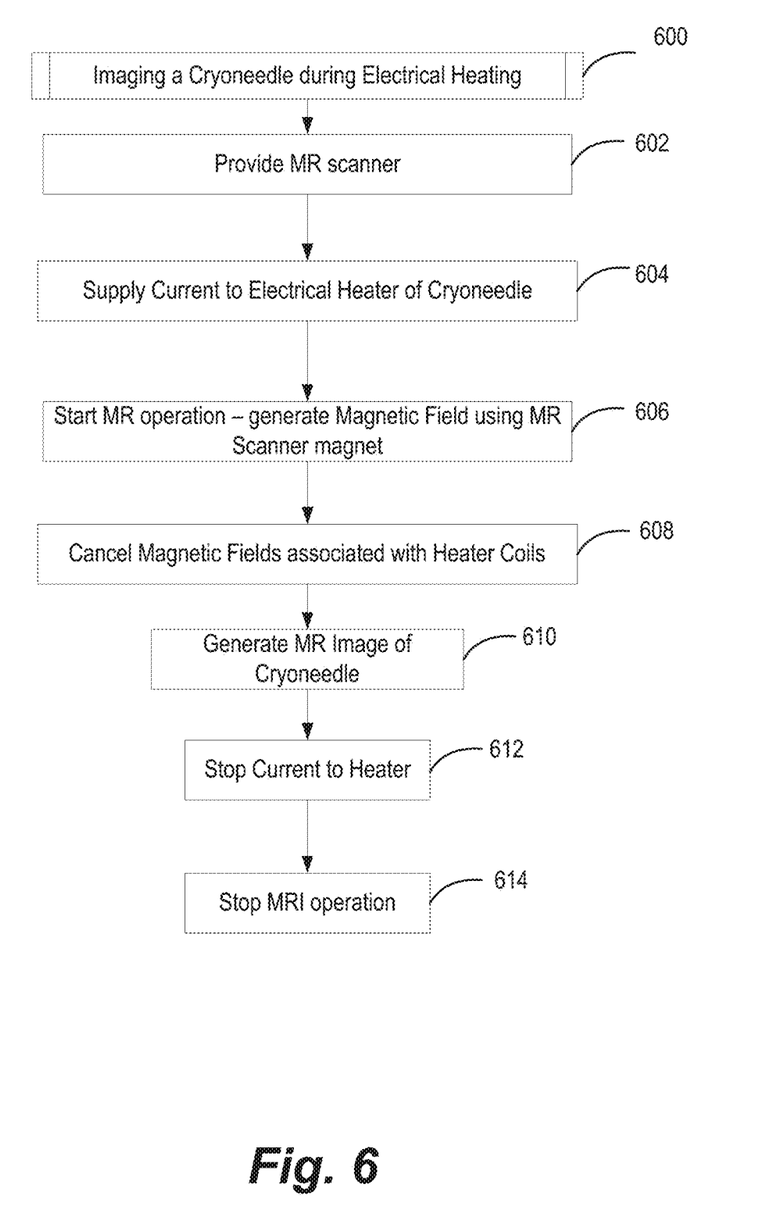
FIG. 6 is a flow chart illustrating a method of imaging a cryoprobe having an electrical heater using magnetic resonance imaging when the probe shaft is being heated.

FIG. 6 illustrates a method 600 of imaging a cryoprobe 100 using magnetic resonance imaging (MRI). The method illustrated in FIG. 6 can be performed with the cryoprobe 100 according to any of the embodiments described herein. Further, the MRI system usable with the method of FIG. 6 can also be according to any of the embodiments described herein. The method can involve the step of providing a MR scanner at step 602. The method involves heating the cryoprobe 100 by supplying current (e.g., using the control system 40) to the electrical heater 116 at step 604. The MR scanner may generate MR signals (such as magnetic field and/or RF signals 202 seen in FIG. 1) at step 606. At step 608, the magnetic fields associated with the heater coils 124A, 124B may be cancelled (e.g., by the first set of coils 124A and the second set of coils 124B, as described above). The cryoprobe 100 can be imaged at step 610 concurrently while the cryoprobe 100 is being heated. Once the desired degree of heating is achieved, the current flow to the heater 116 can be stopped at step 612, and MRI operation can be stopped at step 614.

Notably, the specific sequence of steps of method 500 shown in FIG. 5 and method 600 shown in FIG. 6 should not be construed as limiting, and the steps may be performed in any desired order. For instance, the MR operation may be started before the cryoprobe is inserted into the patient. However, regardless of the sequence of steps that define the method 500 and method 600, in advantageous aspects of the present disclosure, MRI operation may be concurrent and/or simultaneous with the cryoprobe heating operation. The MR magnet may start imaging portions of the cryoprobe before, during or after insertion into the patient, and may continue imaging portions of the cryoprobe inserted into the patient when the electrical heater receives electric current. Such advantages are realized in certain embodiments of the present disclosure as a result of selection of low susceptibility materials for the probe shaft and the electrical heater, and counter-wound helical coils that form the electrical heater.

As described elsewhere herein, aspects of the present disclosure minimize image artifacts that can occur when conventional cryoprobes are used in conjunction with MRI operation. Further, aspects of the present disclosure can also minimize (or eliminate) solenoid effect that may occur when cryoprobes are heated using electrical heaters. In addition, aspects of the present disclosure can also minimize (or eliminate) net forces and/or torques that may act on the probe shaft when cryoprobes with electrical heaters are used in conjunction with MRI systems.

Various examples have been described. These and other examples are within the scope of the following claims.

The invention claimed is:

1. A cryoprobe, comprising:
   a probe shaft having a proximal section and a distal section opposite to the proximal section, the distal section being insertable into a patient, the probe shaft being made of a first material having a magnetic susceptibility of less than about 0.001 in S.I. units;
   a cryofluid supply tube located within the probe shaft, the cryofluid supply tube being configured to receive a cryofluid from a cryofluid source, the cryofluid supply tube being configured to supply the cryofluid toward the distal section for cooling and/or freezing patient tissue; and
   an electrical resistance heater wound around the cryofluid supply tube and comprising resistive elements having counter-wound helical coils located within the probe shaft, the counter-wound helical coils comprising a first set of coils wound in a direction counter to a second set of coils such that the first and second sets of coils are abutting and axially interspaced along the cryofluid supply tube, a number of coils of the first set of coils being balanced by a number of coils of the second set of coils such that when a single current is supplied to the electrical resistance heater, a first magnetic field generated by the first set of coils is counteracted and/or opposite to a second magnetic field generated by the second set of coils, the electrical resistance heater being made of a second material having a magnetic susceptibility less than about 0.0005 in S.I. units, the electrical resistance heater being configured to heat and thereby thaw, and/or cauterize tissue, when current is supplied thereto,
   whereby the electrical resistance heater is configured to provide electrical resistive heating of tissue when positioned in a magnet room of a magnetic resonance imaging (MRI) system.

2. The cryoprobe of claim 1, wherein the first set of coils and the second set of coils are each configured to generate heat when current is supplied to the electrical resistance heater.

3. The cryoprobe of claim 1, wherein the electrical resistance heater comprises a single wire made of the second material, the single wire being wound in a first direction to form the first set of coils, the single wire being wound in a second direction to form the second set of coils, the first direction being counter to the second direction.

4. The cryoprobe of claim 3, wherein the single wire is wound as a continuous loop having a looped section, so as to form the first set of coils and the second set of coils.

5. The cryoprobe of claim 4, wherein the looped section is positioned in or near the distal section of the probe shaft.

6. The cryoprobe of claim 1, wherein the probe shaft is made of Inconel alloys.

7. The cryoprobe of claim 6, wherein the second material is titanium.

8. The cryoprobe of claim 1, wherein the electrical resistance heater is configured to receive electric current when the cryoprobe is connected to an MRI scanner.

9. The cryoprobe of claim 8, wherein the first magnetic field associated with the first set of coils counteract the second magnetic field associated with the second set of coils when current is passing through the electrical resistance heater and the cryoprobe is proximal to the MRI scanner, so as to reduce artifacts in an MRI image generated by the MRI scanner.

10. The cryoprobe of claim 8, wherein the counter-wound helical coils permit cancellation of a first force of the first set of coils and a second force of the second set of coils when current is passing through the electrical resistance heater when the cryoprobe is proximal to the MRI scanner so as to reduce torque on the cryoprobe.

11. The cryoprobe of claim 1, wherein each of the cryofluid supply tube and the electrical resistance heater is coaxial with the probe shaft, the electrical resistance heater being radially offset from an inner wall of the probe shaft so as to form an annular return lumen, the annular return lumen permitting return of the cryofluid from the distal section toward the proximal section.

12. The cryoprobe of claim 1, wherein the electrical resistance heater is connectable to a temperature monitoring and/or control system so as to determine temperature of the electrical resistance heater when current is supplied therethrough.

13. The cryoprobe of claim 1, wherein the first material has a magnetic susceptibility of less than or equal to about 0.0006 in S.I. units.

14. The cryoprobe of claim 1, wherein the second material has a magnetic susceptibility of less than or equal to about 0.0002 in S.I. units.

15. A method of electrically heating a cryoprobe in conjunction with magnetic resonance imaging, comprising:
providing the cryoprobe, comprising:
a probe shaft having a proximal section and a distal section opposite to the proximal section, the probe shaft being made of a first material having a magnetic susceptibility less than about 0.001 in S.I. units, and
an electrical resistance heater comprising resistive elements having counter-wound helical coils such that first and second sets of coils are adjoined abutting and axially interspaced within the probe shaft, the counter-wound helical coils comprising a first set of coils wound in a direction counter to a second set of coils, the electrical resistance heater being made of a second material having a magnetic susceptibility less than about 0.0005 in S.I. units;
placing a patient, including patient target tissue, inside a bore of an MRI system;
inserting the distal section of the cryoprobe into the patient; and
heating the cryoprobe via the electrical resistance heater while the patient is placed in the bore of the MRI system whereby a first magnetic field associated with the first set of coils being counteracted by and/or is opposite to a second magnetic field associated with the second set of coils.

16. The method of claim 15, further comprising thawing the patient target tissue by supplying current to the electrical resistance heater so as to achieve a tissue temperature of between about 60° C. and about 90° C.

17. The method of claim 16, further comprising cauterizing the patient target the tissue by supplying current to the electrical resistance heater so as to achieve a tissue temperature of about 100° C.

18. The method of claim 15, further comprising connecting the electrical resistance heater to a temperature monitoring and/or control system, and measuring temperature of the electrical resistance heater when current is supplied thereto.

19. The method of claim 15, further comprising positioning the cryoprobe in an MRI room comprising the MRI system.

20. The method of claim 15, further comprising cooling and/or freezing tissue by supplying cryofluid to the cryoprobe.

21. The method of claim 15, further comprising cancelling the first magnetic field associated with the first set of coils with the second magnetic field associated with the second set of coils when current is passing through the electrical resistance heater when the cryoprobe is proximal to a MRI scanner, and thereby suppressing artifacts in an MRI image generated by the MRI scanner.

22. The method of claim 21, further comprising cancelling a first force of the first set of coils with a second force of the second set of coils when current is passing through the electrical resistance heater when the cryoprobe is proximal to the MRI scanner, and thereby reducing torque on the cryoprobe.

23. The method of claim 15, wherein, when current is passing through the electrical resistance heater and the cryoprobe is proximal to the MRI system, solenoidal effects are reduced so as to reduce artifacts in an MRI image generated by the MRI system, and when the electrical resistance heater operates simultaneously with the MRI system, a resulting magnetic field induced from the MRI system operating is reduced.

24. The method of claim 15, wherein when current is supplied to the electrical resistance heater concurrently when the probe shaft is positioned proximal to the MRI system when the MRI system is being operated, the electrical resistance heater reduces net forces or torques acting on the probe shaft.

25. A method of imaging a cryoprobe using magnetic resonance imaging (MRI), comprising:
providing the cryoprobe, comprising:
a probe shaft having a proximal section and a distal section opposite to the proximal section, the probe shaft being made of a first material having a magnetic susceptibility less than about 0.001 in S.I. units, and
an electrical resistance heater comprising resistive elements having counter-wound helical coils, the counter-wound helical coils comprising a first set of coils wound in a direction counter to a second set of coils such that the first and second sets of coils are abutting and axially interspaced within the probe shaft, the electrical resistance heater being made of a second material having a magnetic susceptibility less than about 0.005 in S.I. units;
providing a magnetic resonance (MR) scanner;
heating the cryoprobe via the electrical resistance heater by supplying current thereto;
generating MR signals; and
imaging the cryoprobe concurrently when the cryoprobe is being heated, whereby a first magnetic field generated by the first set of coils is counteracted by and/or opposite to a second magnetic field generated by the second set of coils.

* * * * *